(12) United States Patent
Tice et al.

(10) Patent No.: US 6,565,875 B2
(45) Date of Patent: *May 20, 2003

(54) MICROCAPSULES FOR ADMINISTRATION OF NEUROACTIVE AGENTS

(75) Inventors: Thomas R. Tice, Indian Springs, AL (US); David W. Mason, Birmingham, AL (US); Amanda McRae-McFarlane, Birmingham, AL (US); Annica Dahlstromm, Askim (SE); Deborah L. Dillon, deceased, late of Helena, AL (US); Ramon Edens, executor, Chattanooga, TN (US)

(73) Assignee: Southern Research Institute, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/934,382

(22) Filed: Aug. 21, 2001

(65) Prior Publication Data

US 2002/0094347 A1 Jul. 18, 2002

Related U.S. Application Data

(63) Continuation of application No. 08/268,177, filed on Jun. 29, 1994, which is a continuation-in-part of application No. 08/033,309, filed on Mar. 15, 1993, now Pat. No. 5,360,610, which is a continuation of application No. 07/525,383, filed on May 16, 1990, now abandoned.

(51) Int. Cl.$^7$ .............................. A61F 2/02; A61K 9/50
(52) U.S. Cl. ..................... 424/426; 424/501; 424/502
(58) Field of Search .................. 424/426, 501, 424/502

(56) References Cited

U.S. PATENT DOCUMENTS

| | | | |
|---|---|---|---|
| 4,832,686 A | | 5/1989 | Anderson |
| 4,883,666 A | * | 11/1989 | Sabel et al. .................. 424/426 |
| 4,962,091 A | | 10/1990 | Eppstein et al. |
| 4,994,281 A | | 2/1991 | Muranishi et al. |
| 5,225,205 A | | 7/1993 | Orsolini |
| 5,360,610 A | | 11/1994 | Tice et al. |

FOREIGN PATENT DOCUMENTS

| | | |
|---|---|---|
| DE | 4023134 | 1/1991 |
| EP | 0058481 | 8/1982 |
| EP | 0145240 | 6/1985 |
| EP | 0251631 | 1/1988 |
| EP | 0377477 | 7/1990 |
| EP | 0412554 | 2/1991 |
| JP | 60048923 | 3/1985 |
| WO | WO 90/15637 | 12/1990 |
| WO | WO 91/17772 | 11/1991 |

OTHER PUBLICATIONS

Emmett et al. Visualization of migration of transplated astrocytes using polystyrene microspheres. *Brain Res.* 447:223–233 (1988).
Howard et al. "Intracerebral drug delivery in rats with lesion–induced memory deficits," *J. Neurosurg.*, 71:105–112 (1989).
Maulding "Prolonged delivery of peptides by microcapsules," *J. Controlled Release*, 6:167–176 (1987) (abstract).
McRae–Degueurce et al. "Implantable microencasuled dopamine (DA): a new approach for slow–release DA delivery into brain tissue," *Neuroscience Letters*, 92:303–309 (1992).

* cited by examiner

*Primary Examiner*—Carlos A. Azpuru
(74) *Attorney, Agent, or Firm*—Needle & Rosenberg, P.C.

(57) ABSTRACT

The present invention relates to polymeric microspheres as injectable, drug-delivery vehicles for use to deliver bioactive agents to sites within the central nervous system, and for the stimulation of nerve fiber growth by implanting such microspheres within the central nervous system of a patient. Microspheres of less than 45 $\mu$m, preferably less than about 20 $\mu$m, and preferably about 0.1 $\mu$m to about 10 $\mu$m in mean diameter according to the present invention are also selectively taken-up and into astrocytes when delivered directly into the nervous tissues.

25 Claims, No Drawings

MICROCAPSULES FOR ADMINISTRATION OF NEUROACTIVE AGENTS

This application is a continuation of U.S. application Ser. No. 08/268,177, filed Jun. 29, 1994, now allowed, which is a continuation-in-part of U.S. application Ser. No. 08/033,309, filed Mar. 15, 1993, U.S. Pat. No. 5,360,610, which is a continuation of U.S. application Ser. No. 07/525,383, filed May 16, 1990, abandoned. All of the above applications are hereby incorporated by this reference in their entireties for all of their teachings.

It has long been recognized that delivering a drug to its therapeutic site of action within the central nervous system can be a very difficult task because of the numerous chemical and physical barriers which must be overcome in order for such delivery to be successful. A number of methods have been designed to overcome some of these barriers to central nervous system drug delivery as, for instance, the use of liposomes to surmount the blood-brain barrier. However, the disadvantages of a liposome delivery system, including low drug loadings, short duration of action, limited ways to manipulate the rate of drug release, poor storage stability, and problems with scale-up, have precluded the use of such a system. Another method to overcome some of the barriers to central nervous system drug delivery consists of chemically modifying the active drug to a form, called a prodrug, that is capable of crossing the blood-brain barrier, and once across this barrier the prodrug reverts to its active form. One example of such a prodrug delivery system consists of the neurotransmitter dopamine attached to a molecular mask derived from the fat-soluble vitamin niacin. The modified dopamine is taken up into the brain where it is then slowly stripped from its prodrug mask to yield free dopamine.

The most common method to surmount some of the physical barriers preventing drug delivery to the central nervous system has been through the use of pumps. A variety of pumps have been designed to deliver drugs from an externally worn reservoir through a small tube into the central nervous system. Although such pump delivery systems can be externally controlled to a certain degree, the potential for infection directly within the central nervous system is great and the exact site of action of the drug within the central nervous system is largely beyond control.

To be successful, it does not suffice just to deliver the drug within the central nervous system. The drug must be delivered to the intended site of action, at the required rate of administration, and in the proper therapeutic dose. Commercially, the Alzet osmotic mini-pump has become an acceptable, very useful, and successful means of delivering drugs at a controlled rate and dose over extended periods within the central nervous system. However, adapting this device to deliver the desired drug to discrete brain nuclei presents vast difficulties such as implanting cannulas directly within the designated brain regions.

Still another technique that has been developed to deliver neuro-active agents, such as neurotransmitters, to the central nervous system is with the use of neural transplants. Viable neuronal tissue can be implanted directly within discrete brain nuclei. The duration of substance delivery from the transplanted tissue does not present a problem because implanted tissue may survive for a long time in the host's central nervous system. This technique surmounts a number of obstacles cited above, however, despite claims that neuronal grafts from fetal dopamine cells exhibit some of the autoregulatory feedback properties that are normally found in intact dopamine neuronal systems, the exact rate at which the neurotransmitters are delivered from neuronal transplants at their site of action can not be predetermined.

In 1817, James Parkinson described a disease which he termed "shaking palsy". This condition is presently known as Parkinson's disease and occurs in the middle-aged and elderly. While its onset is insidious, often beginning with tremor in one hand followed by increasing bradykinesia and rigidity, it is slowly progressive and may become incapacitating after several years. In idiopathic Parkinson's disease, there is usually a loss of cells in the substantia nigra, locus ceruleus and other pigmented neurons, and a decrease of dopamine content in axon terminals of cells projecting from the substantia nigra to the caudate nucleus and putamen commonly referred to as the nigrostriatal pathway.

Some symptoms of Parkinson's disease can be treated by the administration of L-3,4-dihydroxyphenylalanine (levodopa or L-dopa). L-dopa, the metabolic precursor of dopamine, is used for replacement therapy because dopamine itself does not cross the blood-brain barrier. However, it must be given in large doses of 3 to 15 grams per day because much of the drug is metabolized before it reaches the site of action in the brain. Alternatively, it is often given in combination with a dopa decarboxylase inhibitor, such as carbidopa, which prevents the metabolism of L-dopa until it crosses the blood-brain barrier. Its greatest effect is on bradykinesic symptoms. After about five years of treatment, side effects develop and the treatment becomes less and less effective even with increasing doses of the drug. These problems have raised the question of whether or not it would be possible to replace the lost dopamine by other means which would deliver the drug to its therapeutic site of action within the central nervous system.

The discovery that a unilateral lesion of the nigrostriatal pathway by the neurotoxin 6-hydroxy-dopamine produced an asymmetry of movement and posture in the rat, provided an animal model for Parkinson's disease. This asymmetry of movement is employed in the rotometer model developed to measure rotational behavior induced by drugs that interfere with dopamine neurotransmission such as apomorphine. The characteristic apomorphine-induced rotational behavior is only observed in animals with a 90 to 95% reduction of dopamine levels in the striatum, and replacement dopamine in this tissue either by transplants of fetal dopamine-producing cells or adrenal medullary tissue results in significant decreases in apomorphine-induced rotational behavior.

Even though these approaches are well documented for experimental animal models, their use as therapy for neurodegenerative disorders such as Parkinson's disease present a number of practical as well as ethical considerations. Not only is the use of human aborted fetal tissue a controversial issue, but this technique involves complicated surgical procedures. Furthermore, although clinical trials of adrenal and fetal tissue implants in Parkinsonian patients are being conducted, the mechanism and long-term efficacy of tissue transplants within the nervous system remain unclear and is still a matter of medical debate. The best theoretical approach for treatment of such central nervous system pathologies continues to be one which would deliver the biologically active agent directly to the damaged region of the central nervous system.

Although a number of different methods have been proposed and are presently being utilized for the delivery of pharmaceutically active compounds to the central nervous system (as used herein, "nervous system" and "central nervous system" are generally used interchangeably indicating that although one aspect of the present invention is to provide for a means of delivering a neuro-active agent directly into the central nervous system, another aspect is to provide for uptake of the microspheres according to the present invention by astrocytes wherever they may occur in the nervous system), there are sufficient disadvantages to each method that the need for delivering biologically active substances to the central nervous system still exists. The present invention addresses this need in a unique manner.

Broadly defined, the present invention relates, in part, to microspheres that have been developed as injectable, drug-delivery vehicles in which bioactive agents are contained within a polymer compatible with nerve tissues. As used with regard to the present invention, the term microsphere includes microcapsules, nanocapsules, microparticles, nanoparticles and nanospheres.

Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the selective uptake of microcapsules into astrocytes, the mean average diameter is less than about 45 $\mu$m, preferably less than 20 $\mu$m, and more preferably between about 0.1 $\mu$m and about 10 $\mu$m.

As used in the present invention, the microcapsule, or nanocapsule, has its encapsulated material (in the present invention this is a bioactive agent or drug) centrally located within a unique membrane. This membrane may be termed a wall-forming polymeric material. Because of their internal structure, permeable microcapsules designed for controlled-release applications release their agent at a constant rate (called a "zero order" rate of release). Thus, as used in the present invention, microcapsules include microparticles in general which comprise a central core surrounded by a polymeric membrane.

In addition, microspheres encompass "monolithic" and similar particles in which the bioactive agent is dispersed throughout the particle; that is, the internal structure is a matrix of the bioactive agent and a polymer excipient. Usually such particles release their bioactive agents at a declining rate (a "first order" rate of release), however such particles may be designed to release internal agents within the matrix at a near zero order rate. Thus, as used in the present invention, microspheres also include microparticles in general which have an internal structure comprising a matrix of bioactive agent and polymer excipient. Preferred polymers according to the present invention are biocompatible particles. A more preferred particle according to the present invention is one which is both biocompatible and biodegradable.

One preferred polymer employed in the present invention, poly(lactide-co-glycolide), has a number of advantages which render it unique to the method of the present invention. An advantage of this polymer is that it is similar to materials used in the manufacture of present-day resorbable synthetic sutures. Other advantages that this polymer shares with acceptable polymers according to the present invention is that this material is biocompatible with the tissues of the nervous system, including the central nervous system. Still another advantage is that this material is biodegradable within the tissues of the central nervous system without producing any toxic byproducts of degradation. A still further advantage of this material is the ability to modify the duration of drug release by manipulating the polymer's kinetic characteristics, i.e. by modifying the ratio of lactide and glycolide in the polymer; this is particularly important because of the ability to deliver neuro-active molecules to specific regions of the brain at a controlled rate over a predetermined period of time is a more effective and desirable therapy over current procedures for administration. Microspheres made with this and similar acceptable polymers serve two functions: they protect drugs from degradation and they release drugs at a controlled rate over a predesired time. Although polymers have been previously reported for use in the microencapsulation of drugs, the physical, chemical and medical parameters of the microencapsulating polymer for neuro-active molecules to be used in nervous system implantation (such as implantation within the central nervous system) technique according to the present invention are narrow; there is no general equivalency among polymers which allows a polymer previously used for encapsulation of drugs to be freely exchanged for the polymers used to encapsulate neuro-active molecules for drug delivery to the central nervous system or for cell uptake according to the present invention. This is especially true when the site of utilization is the central nervous system.

Although the specifically named polymers described in the Examples contained within this description meet the criteria necessary for implantation within the central nervous system, other biocompatible, biodegradable polymers and copolymers having advantages having similar properties to poly(lactide-co-glycolide) may be substituted in its place. Examples of preferred polymers having the properties of biocompatibility and biodegradability include poly(lactide-co-glycolide) copolymer; polylactide homopolymer; polyglycolide homopolymer; polycaprolactone; polyhydroxybutyrate-polyhydroxyvalerate copolymer; poly(lactide-co-caprolactone); polyesteramides; polyorthoesters; poly β-hydroxybutyric acid; and polyanhydrides. In addition to polymers having both biocompatibility and biodegradability that are used to synthesize microspheres for delivery of neuroactive agents into the central nervous system, non-biodegradable but biocompatible polymers may be used to synthesize microspheres for the second aspect of the present invention, that is for the uptake of microspheres by astrocytes. Such biocompatible but not biodegradable polymers include polydienes such as polybutadiene; polyalkenes such as polyethylene or polypropylene; polymethacrylics such as polymethyl methacrylate or polyhydroxyethyl methacrylate; polyvinyl ethers; polyvinyl alcohols; polyvinyl chlorides; polyvinyl esters such as polyvinyl acetate; polystyrene; polycarbonates; poly esters; cellulose ethers such as methyl cellulose, hydroxyethyl cellulose or hydroxypropyl methyl cellulose; cellulose esters such as cellulose acetate or cellulose acetate butyrate; polysaccharides; and starches.

Results obtained from a number of studies indicate that implantation of these neuro-active agent-containing microspheres provides a feasible method for prolonged release of the agent into the central nervous system. Moreover, the data obtained from studies involving dopamine as the encapsulated agent indicate that dopamine microsphere preparations have the potential of being employed as a source of transmitter replacement allowing diffusion of the microencapsulated dopamine directly into the central nervous system at a controlled rate for pre-determined periods of time assuring functional significance and at the same time remaining compatible with the central nervous system tissue. However, most surprisingly, the data indicate that microencapsulated dopamine injected into specific regions of the brain has the heretofore unreported ability to cause growth of nerve fibers. Thus, the method of placing the microencapsulated neuroactive agents, manufactured in accordance with one aspect of the present invention, has the potential of promoting the growth of those neural elements which are responsible for the production of endogenous dopamine within the central nervous system. Once growth has taken place and the neural fiber elements have matured and stabilized within their environment, they will continue to produce and release dopamine within the central nervous system thereby providing for the first time a potential cure for Parkinson's disease.

Among the neuro-active molecules or agents which may be microencapsulated and administered according to the present invention are neurotransmitters; neuropeptides; and neurotrophic factors including such agents as norepinephrine; epinephrine; serotonin; dopamine; substance P; somatostatin; nerve growth factor; angiotensin II; corticotropin releasing factor; choline; acetyl choline; cholinergic neuronotrophic agents; basic fibroblast growth factor; acidic fibroblast growth factor; brain derived growth factor; nerve growth factor; insulin growth factor; transforming growth factorβ; epidermal growth factor; transforming growth factor; glial derived growth factor; estrogen; inorganics used for the treatment of depression such as lithium; gamma aminobutyric acid; gamma aminobutyric acid mimetics; oxytocin; phenylethyl amine; and interleukin-1.

Among the neurological conditions which may be treated microencapsulated neuro-active molecules being placed directly within the tissues of the central nervous system are spinal chord injuries, amyotorphic lateral sclerosis, Parkinson's disease, Huntington's Chorea, Alzheimer's disease, epilepsy, and Tardive dyskinesia. Depending upon the disease to be treated, it may be advantageous to provide more than one microencapsulated neurotransmitter, neuropeptide and neurotrophic factor to the central nervous system. For example, as dopamine, cholecystokinin, and epidermal and basic fibroblast growth factors may all be involved in Parkinson's disease, ultimately it may be advantageous when presented with a patient having the disease to provide a mixture of microencapsules containing two, or more neural-active molecules to the central nervous system (see Example 4).

In order to provide a more complete description and provide a greater understanding of the various aspects of the present invention, reference is made to the following examples.

EXAMPLE 1

Preparation of Dopamine Microspheres

A 1 weight percent polymer solution was prepared by dissolving 2 g of 50:50 poly(DL-lactide-co-glycolide) ("DL-PLG") in 198 g of dichloromethane (The DL-PLG had an inherent viscosity of 1.27 dL/g.). Two grams of dopamine (3-hydroxytyramine hydrochloride) were suspended in the polymer solution by homogenization. The dopamine suspension was then poured into 300 ml resin kettle and stirred at 3500 rpm with a 1.5 inch Teflon impeller. Silicone oil (350 cs) was pumped into the resin kettle at a rate of 2 ml per min. After approximately 50 ml of oil was added, the contents of the resin kettle were poured into 3.5 L of heptane. The heptane was stirred at 900 rpm with a 2.5 inch stainless steel impeller. After 0.5 h of stirring, the dopamine microsphere suspension was poured through a stainless steel sieve with 45 µm openings to remove microspheres larger than 45 µm in diameter. Microspheres less than 45 µm in diameter were collected on a fritted glass filter funnel and dried at room temperature in a vacuum oven for 48 h. The dopamine microspheres were then collected in tared glass scintillation vials and stored under desiccant at 4° C.

Dopamine was encapsulated in two types of copolymer excipients made in accordance with Example 1. One copoylmer had a 50:50 mole ratio of lactide to glycolide and the other copolymer had a 65:35 mole ratio. In view of the higher lactide content of the 65:35 copolymer, this copolymer will take longer to biodegrade than the 50:50 copolymer. Thus, the delivery time of the 65:35 copolymer can be longer than the delivery time of the 50:50 copolymer. Additional variations of the actual proportions of lactide and glycolide in the copolymer and the copolymer morphology may be manufactured to more or less custom adjust the rate and amount of neuro-active molecule being released into the central nervous system The final microspheres are free-flowing powders consisting of spherical particles approximately 1 to 45 µm in diameter. These microspheres can easily be suspended in aqueous vehicles and injected through conventional hypodermic needles. Although the amount of dopamine contained in each microsphere may vary, the microspheres manufactured and used in the following example consisted of about 40% (by weight) dopamine and of about 60% (by weight) of the poly(DL-lactide-co-glycolide). When used as a therapeutic, the microspheres may contain from about 1% to about 80% [by weight] dopamine). In vitro diffusion tests of these microspheres showed that most of the dopamine was released into deionized water within 30 minutes. Prior to injection, the microspheres are sterilized with, preferably, gamma radiation.

EXAMPLE 2

Implantation of Microspheres

Microencapsulated dopamine was formulated (15 mg of 50:50 microencapsulated dopamine in 50 µl saline or 30 mg of 65:35 microencapsulated dopamine in 50 µl of saline) for implantation into previously treated rat models.

Male Sprague Dawley rats were unilaterally lesioned in the ascending median forebrain bundle of monoamine neurons using the neurotoxin 6-hydroxy-dopamine. Two weeks later, the animals were challenged with apomorphine (0.1 mg/kg SC) and rotational responses were monitored in a computerized rotometer set-up. Only rats in which the dopamine denervation has been successful will display strong contralateral rotation to apomorphine challenge. Therefore, animals responding to apomorphine with less than 400 contralateral rotations per 60 minutes during the first two weeks of testing were eliminated from the study. Testing of positive responders was then continued on a weekly basis using apomorphine.

Once the animals reached a stable rotational baseline level to dopamine agonist challenge, they were stereotaxically injected under light ether anesthesia with a suspension of dopamine microspheres. Dopamine/50:50 DL-PLG microspheres (15 mg microspheres/50 µL saline) were injected in 3 µl implants into the striatum. Dopamine/65:35 DL-PLG microspheres were correspondingly implanted (30 mg microspheres/50 µL saline) in the striatum. Based upon experience, it was expected that the 65:35 DL-PLG microspheres would biodegrade completely in about 12 weeks, and the 50:50 DL-PLG microspheres would do so in about 6 weeks. Thus, to ensure similar doses of dopamine would be released per unit time, the amount of dopamine in the 50:50 DL-PLG microspheres was half that of the 65:35 DL-PLG microspheres. Control rats received dopamine-free microspheres. Standard Hamilton syringes (50 µl) connected by polyethylene tubing to stainless steel injection cannulae were used for the injections. Upon completion of the injection, the cannula were left in situ for an additional 60 sec before being slowly retracted and the skin wound closed. Starting 1 to 3 days after implantation of the dopamine microspheres, the animals were repeatedly tested for dopamine agonist-induced rotation at various intervals over an 8 week period.

Thirty to forty minutes after intrastriatal implantation of the microencapsulated dopamine, those rats receiving the dopamine/50:50 DLPLG microsphere implantation exhibited contralateral rotations with an amplitude similar to that of a previous test dose of apomorphine but with longer duration. Rats receiving the dopamine/65:35 DL-PLG microsphere implantation displayed a somewhat more protracted response to the implantation, however once begun, these animals have a peak rotation amplitude similar to that of those receiving the dopamine/50:50 DL-PLG microspheres. Empty microspheres were also administered as a control, and these did not modify apomorphine-induced rotational behavior in the rat. Histologic evaluations made upon sacrificed animals indicate that the injection of a suspension of microspheres according to the present invention into the rat brain is an acceptable means of delivering dopamine to the central nervous system; only minimal damage to the surrounding tissue and minimal glial reaction was noted following injection. Thus, there is little concern that a morphological barrier exists which would prevent the diffusion of dopamine into the targeted region.

Thus, we have confirmed our original belief that the specific polymeric microspheres according to the present invention provide a unique and acceptable means to introduce neuro-active molecules into the central nervous system.

The most outstanding result of delivering dopamine to the central nervous system utilizing the method and microspheres of the present invention is finding the presence of dopamine immunoreactive fibers growing towards the dopamine microspheres. This is not seen in control (those microspheres not containing dopamine) microsphere implantation. The ability of implanted dopamine microspheres manufactured and implanted according to the present invention to elicit neuronal sprouting may provide not only a treatment for neurologically debilitating diseases such as Parkinson's disease, but a cure as well.

As part of ongoing research into the direct delivery of neuro-active molecules to the brain, an antibody to dopamine showing no cross reactivity with other neurotransmitter systems (such as norepinephrine, serotonin or gamma amino butyric acid) when utilized in ELISA test systems was developed. This antibody has been shown in both ELISA and immunocytochemical test systems to recognize dopamine and is a reliable means of demonstrating fiber outgrowth in the rat brain as depicted in the following example:

EXAMPLE 3

Fiber Formation

The immunogen complex to obtain antibodies against dopamine is prepared by coupling the hapten to glutaraldehyde (G) and bovine serum albumin (BSA). Rabbits are then immunized with this immunogen. Antibodies directed toward dopamine were detected 50 days following the immunization schedule of 4 injections at 10 day intervals. To eliminate antibodies that are produced against BSA-G, the dopamine antibody was adsorbed by affinity chromatography. In order to visualize dopamine within brain tissue, the rats were perfused with gluteraldehyde thereby fixing dopamine and tissue proteins. Thus, because the antibody is directed against dopamine-gluteraldehyde and a protein, the antibody will recognize this complex within the brain. Rats were deeply anesthetized with sodium pentobarbital and perfused through the aorta with a mixture composed of 5% gluteraldehyde and an anti-oxidant to prevent the rapid release of dopamine from the brain tissue. After the rats were perfused with this mixture, the brains were removed and allowed to equilibrate overnight in 10% sucrose solution. The brains were then frozen, sectioned, and the sections incubated with anti-dopamine antiserum for 24 hours. The following day the sections were reacted with goat anti-rabbit biotin IgG which recognizes the antiserum produced in the rabbit. Following this, the sections were incubated with avidin biotin-peroxidase complex which recognizes the fixed biotin molecules. The peroxidase was then reacted with a classical chromatogen for this type of reaction, 3,3 diaminobenzidine, and the reaction enhanced by the addition of ammonium nickel sulphate giving a purple stain to the antibody reaction. Therefore, the presence of dopamine in the brain tissue is visualized as a purple deposit in the tissue; if dopamine is not present in the tissue, the tissue remains unstained.

In addition to dopamine, noradrenaline was also encapsulated in microspheres according to the present invention and tested as described above with similar results. With noradrenaline-containing microspheres implanted as describe in Example 2, the duration of decreases in apomorphine-induced rotational behavior was longer with noradrenaline encapsulated in 50:50 DL-PLG microspheres as compared to dopamine encapsulated in 50:50 DL-PLG microspheres. In a comparative study 15 weeks post implantation, a 35% decrease (65% of baseline) was observed in animals in which the noradrenaline/50:50 DL-PLG microspheres were implanted; a 40% decrease (60% of baseline) was observed in animals in which the dopamine/65:35 DL-PLG microspheres were implanted; and a <5% (>95% of baseline) was observed in animals that received empty DL-PLG microspheres.

EXAMPLE 4

Neural Fiber Growth Following Implantation of Noradrenaline-Containing Microspheres For the visualization of neural fibers following implantation of the noradrenaline-containing microspheres, an antibody directed against tyrosine hydroxylase, an enzyme found in the rate-limiting step for both dopamine and noradrenaline was used. For tyrosine hydroxylase immunochemistry, the rats were overdosed with sodium pentobarbital and perfusion-fixed with 4% paraformaldehyde as described in Example 3. The brains were post-fixed for 4 h in the paraformaldehyde solution and then immersed overnight in phosphate-buffered saline containing 10% sucrose. Cryostat sections were then incubated overnight with anti-tyrosine hydroxylase antibody (1/800), and further processed by conventional avidin-biotin peroxidase methodology. Tyrosine hydroxlase present in the sections are readily apparent as a purple-colored deposit.

The fiber growth following implantation of noradrenaline microspheres is comparable to that noted after implantation of dopamine microspheres. Ultrastructural results confirmed the presence of tyrosine hydroxylase immunoreactive fibers growing in the striatum up to 4 months following microsphere implantation.

In a similar study, an equal mixture of dopamine encapsulated in 50:50 DL-PLG microspheres and noradrenaline encapsulated in 50:50 DL-PLG microspheres were implanted as described in Example 2. Implanting this mixture of microspheres produced significant reductions in the number of apomorphine-induced rotations for up to 3 months; two animals in the test group displayed an 80% (% baseline) reduction in the number of apomorphine-induced rotations for 4 weeks. Such a dramatic reduction in the number of apomorphine-induced rotations has not been observed in experiments with implantation of microspheres containing only dopamine or noradrenaline.

The following examples are provided to demonstrate alternative polymeric microspheres used in the present invention.

EXAMPLE 5

Preparation of Dopamine Microspheres with Polycaprolactone Using a Phase-Separation Process A 2 weight percent polymer solution was prepared by dissolving 1 g of polycaprolactone in 49 g of dichloromethane. (The polycaprolactone had an inherent viscosity of 1.0 dl/g.) One gram of dopamine (3-hydroxytyramine hydrochloride) was suspended in the resultant polymer solution. The dopamine/polymer mixture was then poured into a 100 ml resin kettle. While stirring the contents of the resin kettle at 3500 rpm with a 1.5-inch Teflon impeller, silicone oil (350 cs) was pumped into the resin kettle at a rate of 0.6 ml per min. After approximately 8 ml of oil was added, the content of the resin kettle was poured into 3 L of heptane. The heptane was stirred at 500 rpm with a 2.5 in. stainless steel impeller. After 0.5 h of stirring, the dopamine microspheres were collected on a fritted glass funnel and dried at room temperature in a vacuum oven for 48 h. The microspheres were processed through a stainless steel sieve with 45 μm openings to remove microspheres larger than 45 μm in diameter. The dopamine microspheres were then collected in tared glass scintillation vials and stored under desiccant at 4° C.

EXAMPLE 6

Preparation of Dopamine Microspheres with Polycaprolactone Using a Solvent-Extraction Process A 20 weight percent polymer solution was prepared by dissolving 1 g of poly-caprolactone in 4 g of dichloromethane. (The polycaprolactone had an inherent viscosity of 1.0 dl/g.) A dispersion was formed by suspending 1 g of dopamine (3-hydroxytyramine hydrochloride) in the polymer solution. An emulsion was formed when the dopamine/polymer dispersion was transferred into a 300 ml resin kettle containing 188 g of process medium stirring at 1200 rpm with a 1.5 in. Teflon impeller. The process medium consisted of 5 wt % poly(vinyl alcohol) and 16 wt % calcium chloride saturated with 4.4 g of dichloromethane. After 1 min of stirring, the dopamine microspheres were hardened by extracting the dichloromethane from the microspheres. This extraction was done by adding the content of the resin kettle to a bath containing 1022 g of a 32 weight percent calcium chloride solution stirring at 200 rpm. At 10 and 20 minutes, this post addition, 500 ml of water were slowly added to the extraction bath. (Total extraction time was 30 min.) The contents of the extraction bath was next centrifuged at 1800×G for 45 min. After centrifugation, the microspheres were collected on a fritted glass funnel and dried at room temperature in a vacuum oven for 48 h. The microspheres were processed through a stainless steel sieve with 45 μm openings to remove microspheres larger than 45 μm in diameter. The dopamine microspheres were then collected in tared glass scintillation vials and stored under desiccant at 4° C.

EXAMPLE 7

Preparation of Dopamine Microspheres with Polyhydroxybutyrate/Polyhydroxyvalerate Copolymer Using a Solvent-Extraction Process A 15 weight percent polymer solution was prepared by dissolving 0.75 g of polyhydroxybutyrate/polyhydroxyvalerate copolymer (PHBV) in 4.3 g of dichloromethane. A dispersion was formed by suspending 1 g of dopamine (3-hydroxytyramine hydrochloride) in the polymer solution. An emulsion was formed when the dopamine/polymer dispersion was transferred into a 300-ml resin kettle containing 179 g of process medium stirring at 1400 rpm with a 1.5-in. Teflon impeller. The process medium consisted of 5 weight percent poly(vinyl alcohol) saturated with 4.3 g of dichloromethane. After 1 min. of stirring, the dopamine microspheres were hardened by extracting the dichloromethane from the microspheres. This extraction was done by adding the contents of the resin kettle to a bath containing 1021 g of water stirring at 740 rpm. After 30 min. of stirring, the microspheres were centrifuged at 1800×G for 45 min. Then, the microspheres were collected on a fritted glass funnel and dried at room temperature in a vacuum oven for 48 h. The microspheres were processed through a stainless steel sieve with 45-μm openings to remove microspheres larger than 45 μm in diameter. The dopamine microspheres were then collected in tared glass scintillation vials and stored under desiccant at 4° C.

EXAMPLE 8

Preparation of Norepinephrine Microspheres with 55:45 poly(DL-lactide-co-glycolide) Using a Phase Separation Process A 2 weight percent polymer solution was prepared by dissolving 3 g of 55:45 DL-PLG in 150 g of dichloromethane (the DL-PLG has an inherent viscosity of 1.0 dL/g). Three grams of norepinephrine was suspended in the resultant polymer solution. The norepinephrine/polymer mixture was then poured into a 250 ml glass beaker and maintained at 20° C. in an ice bath. While stirring the contents of the beaker at 4500 rpm with a Silverson emulsifier, silicone oil (350 cs) was pumped into the beaker at a rate of 1.9 ml per minute. After approximately 47 ml of oil was added, the contents of the beaker was poured into 4.5 L of heptane. The resulting mixture was stirred at 1000 rpm with a 2.5 in. stainless steel impeller. After 30 mins. the norepinephrine microspheres were collected on a fritted-glass funnel and dried at room temperature in a vacuum oven for 48 hrs. The microspheres were processed through a stainless steel sieve with 45 μm openings to remove microspheres larger than 45 μm in diameter.

EXAMPLE 9

In vitro Release Method

About 10 mg of dopamine microspheres were weighed into a polystyrene culture tube (17-mm by–100 mm), then 6 ml of receiving fluid (distilled water) was added to the culture tube. A serum filter (16-mm by 4-mm) was placed in the culture tube, and the bottom edge of the filter was positioned just above the surface of the receiving fluid. The resultant assembly was stationed in a test-tube rack and then placed in an incubator maintained at 37° C.

A receiving fluid sample was collected by depressing the filter to the bottom of the culture tube until as much of the receiving fluid as possible was pushed above the filter. This receiving fluid was then reserved for dopamine quantification. Then 6 ml of fresh receiving fluid was transferred to the culture tube, and the filter was repositioned above the receiving fluid. The assembly was returned to the incubator until the next sample was collected. In vitro release samples were collected at 15, 30, 45, 60, 120, 240 and 1440 min. The samples were quantified for dopamine spectrophotometrically at 292 nm.

As noted in Example 2, the implantation of control microspheres did not modify the apomorphine-induced rotational responses in the rat, indicating at least a 95% decrease of dopamine in the central nervous system. Microscopic observations of the tissues following staining in accordance with Example 3 confirmed that dopamine was absent in the striatum of the rats receiving the control microspheres, that is the brain tissue remained unstained. However, in animals that received the dopamine microspheres and displayed a continued decrease in apomorphine rotational behavior, microscopic observations indicated dopamine was present both in the microcapsules and the tissue. As noted previously, numerous fine fiber extensions were seen growing towards the implanted microspheres, and dopamine was present in these fibers. These findings indicate that dopamine nerve fibers were growing within the host animal's central nervous system, a phenomena heretofore unreported. The implanted dopamine containing microspheres apparently have the ability to elicit growth of nerve fibers from the ventral portion of the brain toward the microspheres. These fibers were present in all animals which displayed a continued decrease in the number of apomorphine-induced rotations which appears to be due to a release of dopamine from the microspheres as well as the growing dopamine fibers within the host's central nervous system. Similar observations were noted for both the 50:50 DL-PLG and 65:35 DL-PLG dopamine microspheres.

The anatomical placement of the dopamine microspheres appears to be important for both fiber growth and functional recuperation. One rat striatum is about 3 mm in width and 4 mm in depth. Dopamine fibers growing from the ventral portion of the brain are mainly located in the more medial ventral portion of the striatum in comparison to the extreme lateral portion of this nucleus. Placing dopamine microspheres at the ventral portion of the brain stimulates growth of these particular fibers. It appears that the diffusion of dopamine from these microspheres placed in this location reaches these fibers and they grow towards the microspheres. The extreme lateral placement of dopamine containing microspheres therefore appears too distant to allow dopamine diffused from the microspheres to influence these fibers.

Immunocytochemical investigations with an antibody to growth associated protein, a protein associated with systems undergoing fiber growth, indicated the growing fibers were reactive to this protein, an indication that the nerve fibers are undergoing a fiber growth. Injection of fluorogold within the denervated striatum 2 weeks after implantation of dopamine microspheres indicates retrograde labeling of neurons within the ventral tegmentum region, suggesting that the dopamine microspheres trigger the growth of dopamine fibers.

Another observation of growth of fibers has been made when the microspheres were implanted into the striatum of a genetic mouse model. The Weaver mouse strain carries an autosomal recessive mutation and provides investigators a means to investigate fiber growth following dopamine microsphere implantation into a brain region where dopamine is "naturally" depleted. These genetically aberrant mice are severely depleted of their brain dopamine. The abnormality is particularly marked in the nigrostriatal dopamine tract while the mesolimbic dopamine neurons appear less affected. Implanting dopamine microspheres within the striatum of this mouse model equally stimulates the growth of dopamine fibers in the striatum probably emanating from the genetically unaffected dopamine system.

Microscopic observations of the rat brain tissues following the administration of microspheres according to the present invention, confirmed that dopamine was absent in the striatum of the rats receiving the empty microspheres. However, in animals that received the dopamine microspheres and displayed a continued decrease in apomorphine rotational behavior, microscopic observations indicated dopamine was present in both the microspheres and the tissue. Similar results were observed in animals that received the noradrenaline microspheres. Numerous fine fiber extensions were seen growing within the host animal's central nervous system.

While electron microscopic observations revealed the presence of immunoreactive dendrites making postsynaptic contacts with immunonegative axons, this study also demonstrated a most unexpected finding: the microspheres were being taken up by astrocytes within the host animal's nervous tissue. Astrocyte-derived factors regulate neuronal survival, biochemical maturation and morphological differentiation in vitro. The diverse neuronotrophic effects of astrocytes suggest that these cells may express soluble and/or membrane associated molecules with a spectrum of biological activities. The finding that neuroactive-containing microspheres are present within astrocytes may thus explain the neural fiber growth promoting effects observed with microspheres according to the present invention.

In view of these unexpected findings, a study was conducted in vitro to confirm what was observed in vivo.

EXAMPLE 10

Astrocyte Studies

Astrocytes were originally obtained from the striatum of a one day old rat. The astrocytes were separated from neurons and other nerve cells by passing the dissected tissue through a sterile nylon net. The cells were then grown in a culture flask in serum supplemented culture medium for a week and then transferred to 35 mm culture dishes.

Dopamine microspheres (15 mg) were placed in 10 ml of the culture medium overnight at 37° C. overnight to equilibrate. One ml of stirred medium containing dispersed microspheres was added to the culture dishes and allowed to remain in contact with the astrocyte tissue cultures for one week.

Scanning electron microscope observations of the cells following this culture protocol confirmed that astrocytes take up the microspheres having mean average diameters of from less than about 10 $\mu$m. Although larger size microspheres were not observed with this technique, it is possible that larger diameter microspheres were taken up and thus larger sizes of microspheres are considered as potential modifications and alterations of the present invention.

Following the one week incubation, the culture medium was aspirated, the cells rinsed with phosphate buffered saline, and trypsinated for five minutes. Media containing calf serum was added to the trypsinized cells to stop the reaction. The cells were then centrifuged for 5 minutes and resuspended in 200 μl of culture medium.

Adult rats were denervated with 6-OHDA for one month following known protocols. The rats were then implanted with 2×3 μl of the suspended astrocyte cell culture within two different sites in the striatum.

Twelve weeks post implantation, those animals receiving astrocyte-containing dopamine microspheres showed a 45% decrease (% of baseline) in rotations (see Example 2), whereas those animals receiving astrocytes containing empty microspheres showed approximately a 15% decrease in rotations. These results may be interpreted as indicating that within the central nervous system microspheres taken up by astrocytes may provide a means to assure a more prolonged release of dopamine because the dopamine is actually encapsulated twice in such a system: once within the polymer, and second within the astrocyte cell. The use of astrocytes as a delivery system may enhance fiber growth as these cells are implicated in the production and maintenance of numerous growth factors.

Immunochemistry performed 9 months later revealed fiber growth and the viability of the astrocytes; fiber growth was visualized with anti-tyrosine hydroxylase, and the astrocytes with anti-glial fibrillary protein.

Thus, while we have illustrated and described the preferred embodiment of our invention, it is to be understood that this invention is capable of variation and modification, and we therefore do not wish or intend to be limited to the precise terms set forth, but desire and intend to avail ourselves of such changes and modifications which may be made for adapting the present invention to various usages and conditions. Accordingly, such changes and modifications are properly intended to be within the full range of equivalents, and therefore within the purview of the following claims. The terms and expressions which have been employed in the foregoing specification are used as terms of description and not of limitation, and thus there is no intention, in the use of such terms and expressions, of excluding equivalents of the features shown and described, or portions thereof; the scope of the invention being defined and limited only by the claims which follow.

Having thus described our invention and the manner and process of making and using it in such full, clear, concise, and exact terms so as to enable any person skilled in the art to which it pertains, or with which it is most nearly connected, to make and use the same,

We claim:

1. A method for eliciting neural fiber growth within the central nervous system to treat a patient with a neurologic disease or injury, comprising:
    gaining access to the central nervous system of the patient in need of such a treatment; and
    contacting the central nervous system with microspheres comprising a neuroactive molecule encapsulated within a polymer, wherein the micropsheres comprising an effective amount of neuroactive molecule are capable of eliciting neural fiber growth, said polymer (1) being permeable to the neuroactive molecule agent, (2) being biocompatible with the tissues of the central nervous system, (3) being biodegradable within the tissues of the central nervous system without producing toxic by-products of degradation, and (4) having kinetic characteristics that may be manipulated to allow for the permeation of the neuroactive molecule through the polymer at a controlled rate and a predetermined period of time,
    thereby eliciting neural fiber growth within the central nervous system of the patient.

2. The method of claim 1, wherein the microspheres have a mean diameter of from about 0.1 μm to about 20 μm.

3. The method of claim 1, wherein the microspheres have a mean diameter of from about 0.1 μm to about 10 μm.

4. The method of claim 1, wherein the central nervous system does not include the striatum.

5. The method of claim 1, wherein the contacting step comprises implanting the micropsheres into a specific anatomical region of the central nervous system.

6. The method of claim 1, wherein the contacting step comprises implanting the micropsheres into a specific anatomical region of the central nervous system other than the striatum.

7. The method of claim 1, wherein the polymer is biodegradable within the tissues of the central nervous system.

8. The method of claim 1, wherein the neuroactive molecule comprises a neurotransmitter, a neurotransmitter mimetic, a neuronal receptor agonist, a neuronal receptor antagonist, a neuropeptide, or a neurotrophic factor.

9. The method of claim 1, wherein the neuroactive molecule comprises norepinephrine, epinephrine, serotonin, dopamine, substance P, somatostatin, nerve growth factor, angiotensin II, corticoptropin releasing factor, choline, acetylcholine, cholinergic neuronotrophic agents, basic fibroblast growth factor, acidic fibroblast growth factor, brain derived growth factor, insulin growth factor, transforming growth factor β, epidermal growth factor, transforming growth factor, glial derived aminobutyric acid mimetic, oxytocin, phenethyl amine, or interleukin-1.

10. The method of claim 1, wherein the neuroactive molecule is dopamine or a dopamine mimetic.

11. The method of claim 1, wherein the neuroactive molecule is not dopamine or a dopamine mimetic.

12. The method of claim 1, wherein the polymer comprises a polyesteramide, a polyorthoester, a poly β-hydroxybutyric acid, a polyanhydride, a polydiene, a polyalkylene, a polymethacrylate, a polyvinyl ether, a polyvinyl alcohol, a polyvinyl chloride, a polyvinyl ester, a polycarbonate, a polyester, a cellulose ether, a cellulose ester, a polysaccharide, or starch.

13. A method according to claim 1, wherein the polymer comprises poly(lactide-co-caprolactone) copolymer, polyhydroxybutyrate-polyhydroxyvalerate copolymer, polybutadiene, polymethyl methacrylate, polyhydroxyethyl methacrylate, polyvinyl acetate, methyl cellulose, hydroxyethyl cellulose, hydroxypropyl methyl cellulose, cellulose acetate, or cellulose acetate butyrate.

14. The method of claim 1, wherein the polymer comprises a poly(lactide-co-glycolide) copolymer, a polylactide homopolymer, or a polyglycolide homopolymer.

15. The method of claim 1, wherein the microsphere comprises two or more groups of microspheres, wherein each group contains a different neuroactive molecule.

16. The method of claim 1, wherein the neuroactive molecule is dopamine and the polymer is a poly(lactide-co-glycolide) copolymer.

17. The method of claim 1, wherein the neuroactive molecule is dopamine and the polymer is a polycaprolactone.

18. The method of claim 1, wherein the neuroactive molecule is dopamine and the polymer is a polyhydroxybutyrate-polyhydroxyvalerate copolymer.

19. The method of claim 1, wherein the neuroactive molecule is noradrenaline and the polymer is a poly(lactide-co-glycolide) copolymer.

20. The method of claim 1, wherein the neuroactive molecule is norepinephrine and the polymer is a poly(lactide-co-glycolide) copolymer.

21. The method of claim 1, wherein the neuroactive molecule is from 1% to 80% by weight of the microsphere.

22. The method of claim 1, wherein the treatment is for a patient with a neurologic disease and the neurologic disease is Parkinson's disease, amyotrophic lateral sclerosis, Huntington's chorea, Alzheimer's disease, epilepsy, or tardive dyskinesia.

23. The method of claim 1, wherein the treatment is for a patient with a neurologic injury and the neurologic injury is a spinal cord injury.

24. The method of claim 1, wherein the central nervous system is brain tissue.

25. The method of claim 1, wherein the central nervous system is spinal cord tissue.

* * * * *